US00PP29753P3

(12) United States Plant Patent
Suphachadiwong

(10) Patent No.: US PP29,753 P3
(45) Date of Patent: Oct. 16, 2018

(54) ***VANDA* PLANT NAMED 'SPCDW1602'**

(50) Latin Name: ***Vanda* spp. Jones ex R. Br.**
Varietal Denomination: SPCDW1602

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 0 days.

(21) Appl. No.: 15/731,661

(22) Filed: Jul. 13, 2017

(65) Prior Publication Data

US 2018/0042163 P1 Feb. 8, 2018

(30) Foreign Application Priority Data

Aug. 8, 2016 (QZ) ..... PBR 2016/1932

(51) Int. Cl.
*A01H 5/02* (2018.01)

(52) U.S. Cl.
USPC ..... Plt./311
CPC ..... *A01H 5/02* (2013.01)

(58) Field of Classification Search
USPC ..... Plt./311
CPC ..... A01H 5/02; A01H 6/62
See application file for complete search history.

*Primary Examiner* — June Hwu
(74) *Attorney, Agent, or Firm* — Samuel R. McCoy, Jr.

(57) ABSTRACT

A new and distinct *Vanda* cultivar named 'SPCDW1602' which is characterized by light pink sepals and lateral petals which are margined with a darker shade of pink, sepals and lateral petals with purple reticulate venation, a labellum with a dark pink central lobe and light pink lateral lobes, a light pink column, and the stability of these characteristics from generation to generation.

4 Drawing Sheets

Latin name of the genus and species: The Latin name of the genus and species of the novel variety disclosed herein is *Vanda* spp. Jones ex R. Br.

Variety denomination: The inventive variety of *Vanda* disclosed herein has been given the variety denomination 'SPCDW1602'.

CROSS REFERENCE TO RELATED APPLICATIONS

This application claims priority to the Community Plant Variety Rights application number 2016/1932, filed Aug. 8, 2016, which is herein incorporated by reference.

BACKGROUND OF THE INVENTION

Parentage: The *Vanda* variety 'SPCDW1602' originated as a naturally occurring, whole-plant mutation of *Vanda* 'SPCDW0902' (U.S. Plant Pat. No. 23,343), a variety developed and owned by the inventor. The inventor of 'SPCDW1602' is a commercial ornamental plant producer and regularly discovers *Vanda* mutations at his greenhouse operation in Bangphra, Thailand. For said mutations which seem to exhibit commercial potential, cuttings are taken to produce trial plants which are subsequently grown for evaluation. This process resulted in the selection of a limited number of single plants with commercial potential. Micro propagation of said plants was initiated in the laboratory of breeder and limited amounts of trial plants were grown to the flowering stage, after which the positive characteristics were evaluated again. The variety now called 'SPCDW1602' was initially discovered at the inventor's greenhouse operation in Bangphra, Thailand in June of 2010 as one such mutation of 'SPCDW0902'.

Asexual Reproduction: Asexual reproduction of the new cultivar 'SPCDW1602', by way of mericloning, was first initiated in August of 2010 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through six subsequent generations, the unique features of this cultivar have proven to be stable and true to type.

SUMMARY OF THE INVENTION

The cultivar 'SPCDW1602' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1602'. These characteristics in combination distinguish 'SPCDW1602' as a new and distinct *Vanda* cultivar:

1. *Vanda* 'SPCDW1602' exhibits light pink sepals and lateral petals which are margined with a darker shade of pink; and
2. *Vanda* 'SPCDW1602' exhibits sepals and lateral petals with purple reticulate venation; and
3. *Vanda* 'SPCDW1602' exhibits a labellum with a dark pink central lobe and light pink lateral lobes; and
4. *Vanda* 'SPCDW1602' exhibits a light pink column.

BOTANICAL DESCRIPTION OF THE PLANT

Figure 1:
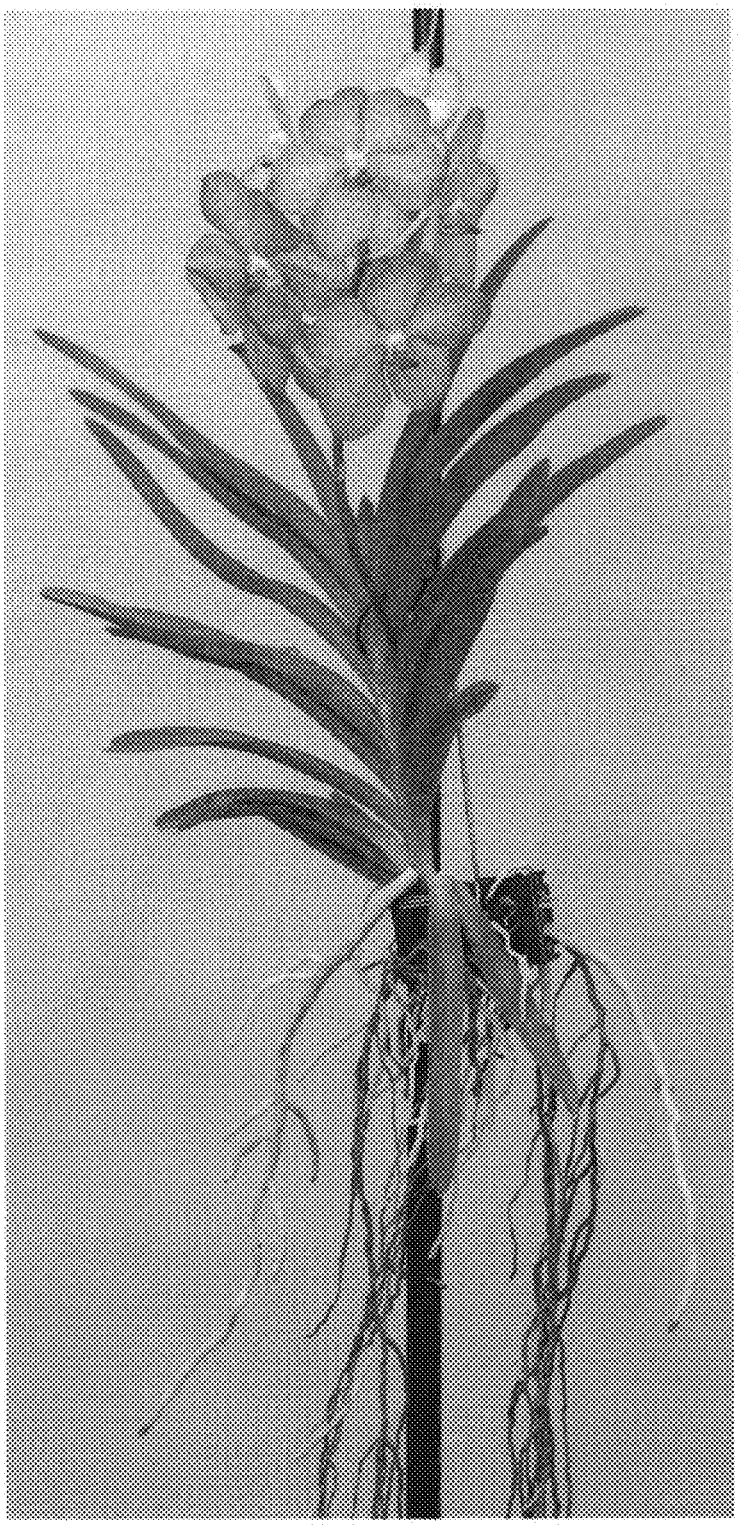
FIG. 1 illustrates, as nearly true as it is reasonably possible to make the same in color photographs of this type, an exemplary plant of 'SPCDW1602' grown in a commercial greenhouse in Honselersdijk, the Netherlands. This plant is approximately 6 years old from the time of mericloning, shown planted in an 8 by 8 cm container.
Figure 2:
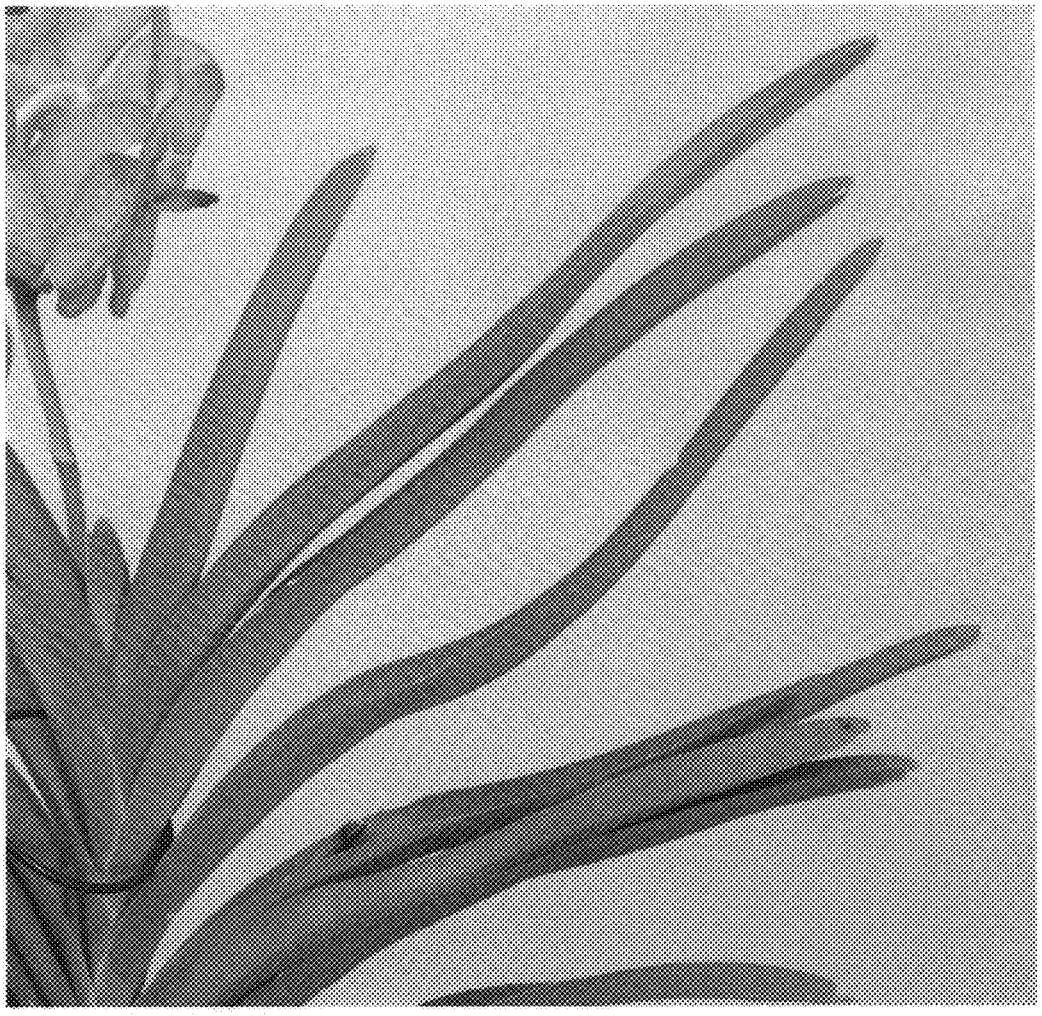
FIG. 2 illustrates, as nearly true as it is reasonably possible to make the same in color photographs of this type, the typical foliage of 'SPCDW1602'.
Figure 3:
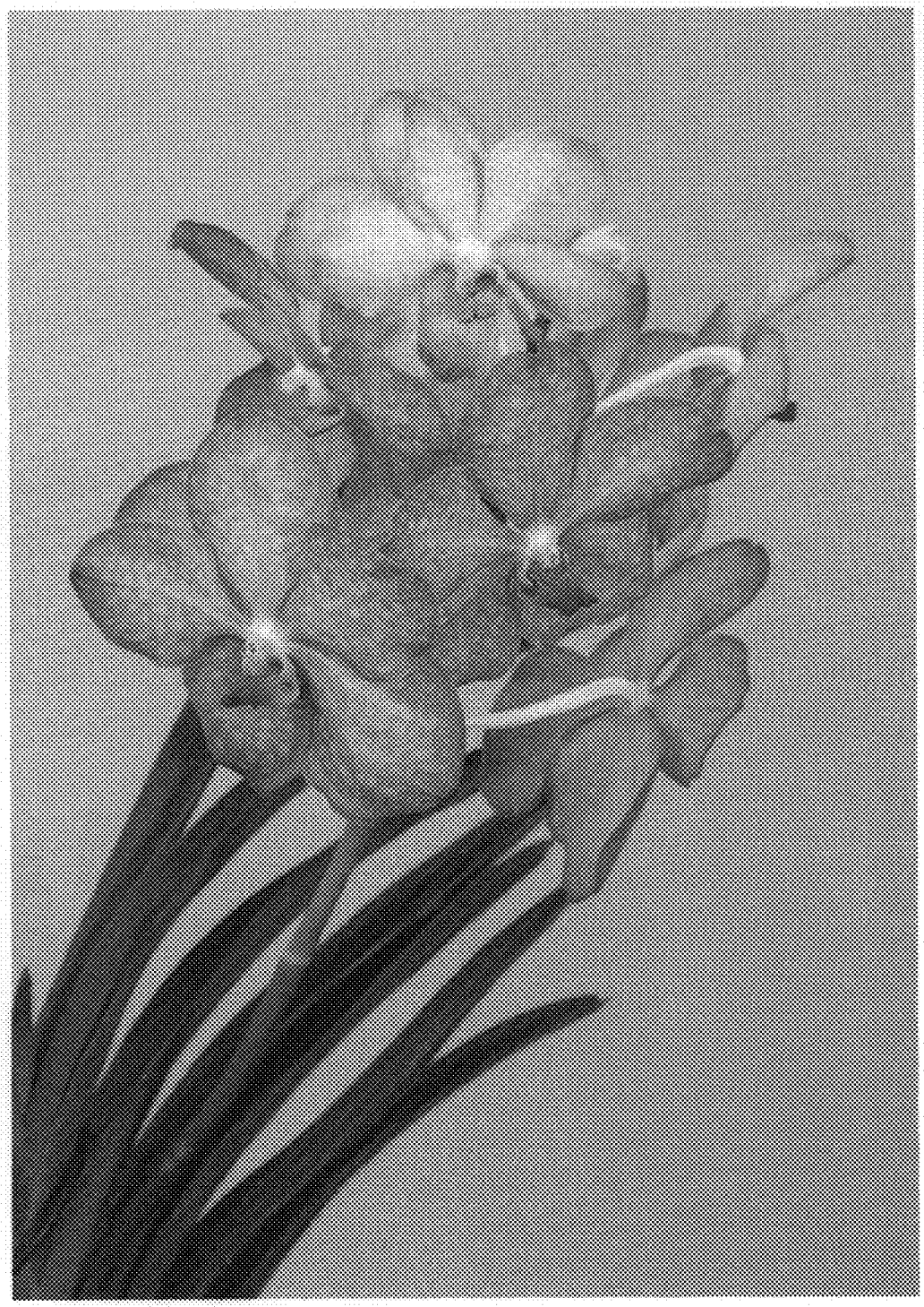
FIG. 3 illustrates, as nearly true as it is reasonably possible to make the same in color photographs of this type, the typical inflorescence of 'SPCDW1602'.
Figure 4:
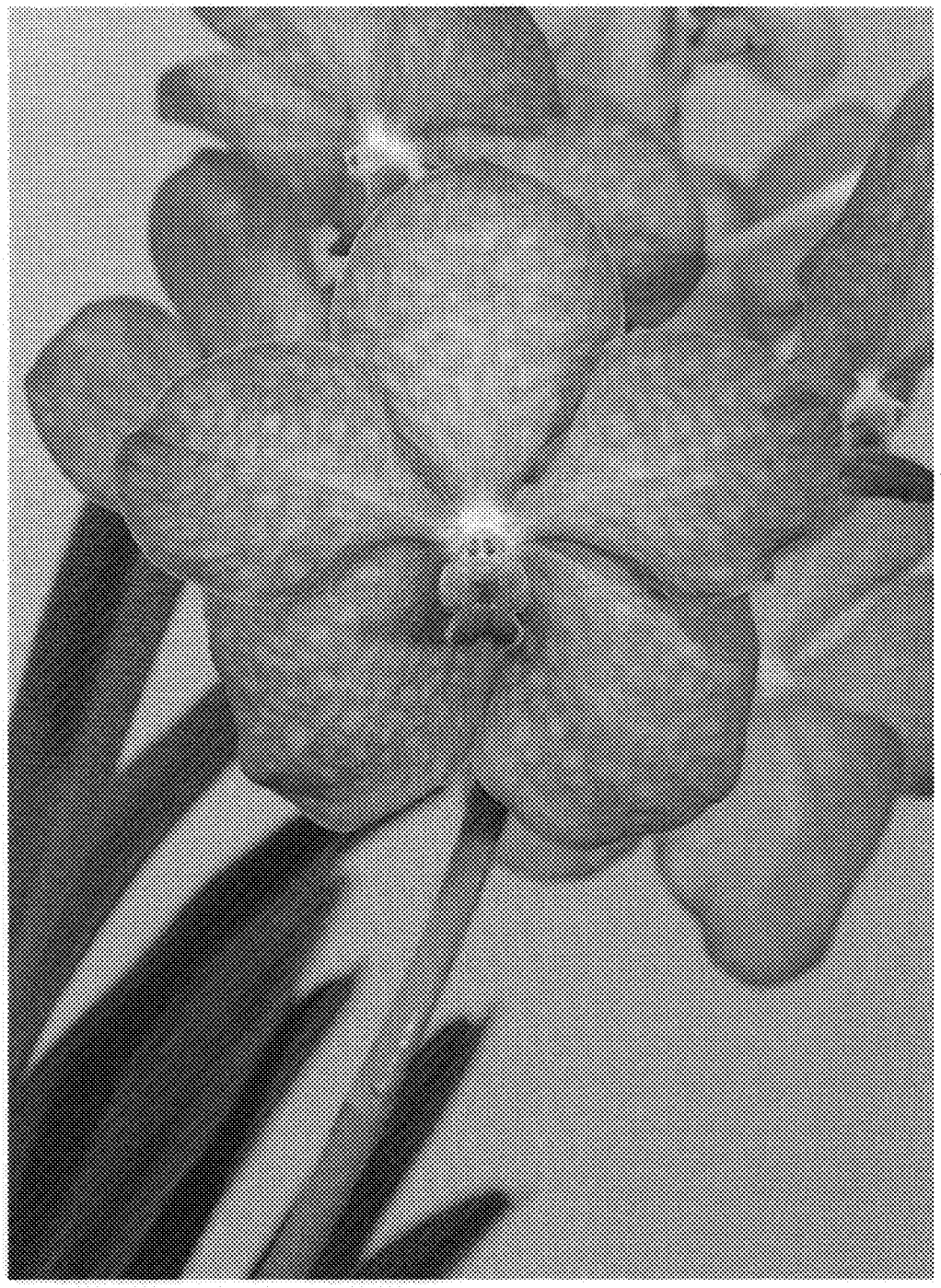
FIG. 4 illustrates, as nearly true as it is reasonably possible to make the same in color photographs of this type, the typical flower of 'SPCDW1602'.

The following observations and measurements made in June of 2017 describe averages from a sample set of six specimens of six year-old 'SPCDW1602' plants grown in a greenhouse in Honselersdijk, the Netherlands. Temperatures were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1602' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart,* The Royal Horticultural Society, London, 2015 (sixth edition).

A botanical description of 'SPCDW1602' and comparisons with the parent and most similar commercial variety of *Vanda* are provided below.

Plant description:

- *Growth habit.*—Perennial; monopodial, upright. Single monopodial leafy stem, with flowers carried slightly above the leaf plane; inflorescences growing from the leaf axils.
- *Average height from base (plant grown in hanging basket, so no soil line present) to foliar plane.*—34.5 cm.
- *Average height from base (plant grown in hanging basket, so no soil line present) to top of floral plane.*—43.8 cm.
- *Plant spread.*—Average of 36.8 cm.
- *Appropriate container size.*—8 cm by 2 cm rectangular hanging basket.
- *Growth rate.*—Moderate.
- *Plant vigor.*—Moderate.
- *Propagation type.*—Meristematic tissue culture propagation using the base of the leaves.
- *Propagation details.*—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.
- *Disease and pest resistance or susceptibility.*—Plants have not been observed to be susceptible or resistant to pathogens and pests common to *Vanda.*
- *Environmental tolerances.*—Adapt to, at least, USDA Zones 11 and 12 and temperatures as high as 40 degrees Celsius; high tolerance to rain; moderate to high tolerance to wind.

Root system:

- *General.*—Sparsely to moderately rooting; with aerial roots only.
- *Dimensions, mature roots.*—41.3 cm long with a diameter of 0.4 cm, on average.
- *Texture.*—Very fleshy; non-fibrous.
- *Color.*—Greyed-green, nearest to in between RHS 193B and 193C; root apex is yellow-green, RHS 143B.

Stem:

- *Branching habit.*—Monopodial; no lateral branches present.
- *Number of primary (main) stems per plant.*—One.
- *Number of secondary (lateral) branches per plant.*—None.
- *Appearance and shape.*—Circular, formed by the leaf sheaths.
- *Length.*—16.5 cm.
- *Diameter.*—0.8 cm.
- *Internode length.*—0.6 cm.
- *Luster.*—Matte.
- *Aspect, main stem.*—Near vertical.
- *Strength.*—Very strong.
- *Color, juvenile.*—Yellow-green, nearest to RHS 145C.
- *Color, mature.*—Yellow-green, nearest to RHS 153D.
- *Color at internodes.*—Yellow-green, nearest to RHS 150D.
- *Pubescence.*—Glabrous.

Foliage:

- *Arrangement.*—Distichous.
- *Dimensions.*—21.3 cm long, excluding the sheath, and 1.9 cm wide.
- *Shape of blade.*—Ligulate; moderately to strongly carinate.
- *Aspect.*—Slightly curved.
- *Apex.*—Unequal praemorse.
- *Base.*—Sheathing.
- *Sheath dimensions.*—2.7 cm long and 1.1 cm wide, on average.
- *Sheath color.*—Yellow-green, nearest to RHS 145C.
- *Margin.*—Entire.
- *Pubescence, texture and luster of adaxial surface.*—Glabrous, smooth, and matte.
- *Pubescence, texture and luster of abaxial surface.*—Glabrous, smooth, and matte.
- *Color.*—Juvenile foliage, adaxial surface — Yellow-green, nearest to RHS 144A. Juvenile foliage, abaxial surface — Green, nearest to RHS 143B. Mature foliage, adaxial surface — Nearest to in between green, RHS 143A, and yellow-green, RHS 146A. Mature foliage, abaxial surface — Yellow-green, nearest to RHS 146B.
- *Venation.*—Parallel.
- *Venation color, adaxial surface.*—Yellow-green, nearest to RHS 144B.
- *Venation color, abaxial surface.*—Yellow-green, nearest to RHS 144B.
- *Petiole.*—No petioles present; leaves sessile.

Inflorescence:

*Inflorescence arrangement*.—Axially placed raceme.

*Natural flowering season*.—Autumn into winter.

*Time to flower*.—Approximately 10 months.

*Flowers per inflorescence*.—Average of 11.

*Flowers per plant*.—10 open flowers and 1 flower buds.

*Inflorescence height*.—Approximately 18.7 cm (measured from base of lowest flower to top of upper flower).

*Inflorescence diameter*.—Approximately 14.4 cm.

*Peduncle*.—Dimensions — Approximately 28.4 cm long and 0.5 cm wide. Aspect — Generally at a 20 degree angle to lateral branch axis; varying between 10 and 30 degrees. Strength — Moderately strong. Texture and luster — Glabrous and slightly glossy. Color — Yellow-green, nearest to RHS 144A.

Bud:

*Length*.—Average of 1.8 cm.

*Diameter*.—Average horizontal diameter is 1.6 cm; the vertical diameter is 1.9 cm.

*Shape*.—Cubic, with a deltoid apex which is pointed downward.

*Pubescence, texture and luster*.—Glabrous, smooth and matte.

*Color*.—Nearest to in between greyed-yellow, RHS 160B, and greyed-green, RHS 195B; apex is purple, nearest to in between RHS 76B and 76C.

Flower:

*Flower type*.—Zygomorphic (orchidaceous), typical shape for the genus *Vanda*.

*Flowering habit*.—Moderately free flowering.

*Shape*.—Zygomorphic, single; consisting of three sepals and three petals, one of which is transformed into a labellum; the two lateral petals slightly to moderately overlap the dorsal and lateral sepals; lateral sepals touching one another.

*Aspect*.—Flowers are outward-facing to slightly nodding.

*Vertical height*.—Approximately 9.0 cm.

*Diameter*.—Approximately 9.0 cm.

*Depth*.—Approximately 2.7 cm.

*Fragrance*.—No fragrance.

*Lastingness*.—3 weeks, on average.

*Persistent*.—Self-cleaning.

*Petals*.—Quantity of Petals — Three unfused petals; two conventional petals and one labellum. Arrangement — One lateral petal on each side. Length — Approximately 4.4 cm. Width — Approximately 3.6 cm. Shape — Obovate. Apex — Obtuse. Base — Cuneate. Margin — Entire; moderately undulated. Pubescence, texture and luster of upper surface — Glabrous, velvety and matte. Pubescence, texture and luster of lower surface — Glabrous, velvety and matte. Color when opening, upper surface — Purple, nearest to in between RHS 76C and 76D, and darker towards the apex, in between RHS 77C and 77D; reticulate venation is purple, nearest to RHS N75A, and darker towards the apex, in between RHS N78B and N78C. Color when opening, lower surface — Purple, nearest to RHS 76D, and darker towards the apex, in between RHS 77C and 77D; reticulate venation is purple, nearest to RHS N78D, and darker towards the apex, in between RHS N78B and N78C. Color when fully opened, upper surface — Purple, nearest to RHS 76C, and darker towards the margins and apex, in between RHS N78B and N78C; base is purple, RHS N77B. Color when fully opened, lower surface — Purple, nearest to RHS 76D, and darker towards the apex, in between RHS N78B, N78C and N78D. Fading, upper surface — Not fading. Fading, lower surface — Not fading. Venation — Densely reticulate. Venation color, fully opened, upper surface — Purple, nearest to RHS N78B, and darker towards the apex, nearest to RHS N78A. Venation color, fully opened, lower surface — Purple, nearest to RHS N78B, and fading to purple-violet towards the apex, nearest to in between RHS N78A and N80A.

*Labellum*.—Shape — Three-lobed; the shape of the lateral lobes is obovate, and the aspect is involute; the shape of the central lobe is oblong, and the aspect is strongly revolute. Length — Central lobe — Approximately 1.8 cm. Lateral lobes — Approximately 0.7 cm. Width — Central lobe — Approximately 0.9 cm at the base and 0.8 at the apex. Lateral lobes — Approximately 0.5 cm. Apex — Central lobe — Deeply emarginate. Lateral lobe — Emarginate. Base — Central lobe — Cuneate. Lateral lobes — Cuneate. Margin — Central lobe — Entire; slightly undulated. Lateral lobes — Entire; not undulate. Texture and luster of upper surface — Central lobe — Glabrous, velvety, and matte. Lateral lobes — Glabrous, velvety, and matte. Texture and luster of lower surface — Central lobe — Glabrous, velvety, and matte, except for apex which is slightly glossy. Lateral lobes — Glabrous, velvety, and matte. Color when opening, upper surface — Central lobe — Proximal half is yellow-green, nearest to RHS 145B and axially striped purple, nearest to RHS N77B; distal half is red-purple, nearest to RHS 71A. Lateral lobes — Yellow-green, nearest to RHS 150D. Color when opening, lower surface — Central lobe — Proximal half is yellow-green, nearest to RHS 145C; distal half is red-purple, nearest to RHS 71A. Lateral lobes — Yellow-green, nearest to RHS 150D, and fading to green-white towards the margins, nearest to RHS 157D. Color when fully opened, upper surface — Central lobe — Proximal half is red-purple, nearest to in between RHS 72A and 72B, and margined lighter, nearest to RHS 70D; distal half is red-purple, nearest to RHS 71A. Lateral lobes — Purple, nearest to in between RHS 76B and 76C. Color when fully opened, lower surface — Central lobe — Proximal half is greyed-yellow, nearest to RHS 160D, and margined purple, nearest to RHS 75D; distal half is red-purple, nearest to in between RHS 70A and 71A. Lateral lobes — Purple, nearest to RHS 76D, and darker towards the apex, nearest to RHS 76B. Fading, upper surface — Not fading. Fading, lower surface — Not fading. Venation — No visible venation. Venation color, fully opened, upper surface — Central lobe — No visible venation. Lateral lobes — No visible venation. Venation color, fully opened, lower surface — Central lobe — No visible venation. Lateral lobes — No visible venation.

*Callosities*.—Dimensions — 1.2 cm long and 0.5 cm wide, on average. Color — Red-purple, nearest to RHS 71A, and fading to purple towards the proximal end, nearest to RHS 76C.

*Spurs*.—Quantity — Average of 1. Length — Approximately 0.8 cm. Diameter — Approximately 0.2 cm. Vertical height — Approximately 0.5 cm, at the base. Shape — Short triangular; flattened. Apex — Bluntly acute. Base — Broad cuneate. Pubescence, texture and luster — Glabrous, smooth, and matte.

Color — Purple, nearest to RHS 75D; striped a darker shade of purple, nearest to in between RHS 75B and 75C.

*Sepals*.—Quantity — Average of 3 unfused sepals. Arrangement — One dorsal sepal and two lateral sepals. Length — Dorsal sepal — Approximately 4.5 cm. Lateral sepals — Approximately 4.7 cm. Width — Dorsal sepal — Approximately 3.8 cm. Lateral sepals — Approximately 4.4 cm. Shape — Dorsal sepal — Broad ovate. Lateral sepals — Broad ovate to near orbicular. Apex — Dorsal sepal — Emarginate. Lateral sepals — Obtuse. Base — Dorsal sepal — Cuneate. Lateral sepals — Cuneate. Margin — Dorsal sepal — Entire; very slightly undulated. Lateral sepals — Entire; moderately undulated. Pubescence, texture and luster, upper surface — Dorsal sepal — Glabrous, velvety, and matte. Lateral sepals — Glabrous, velvety, and matte. Pubescence, texture and luster, lower surface — Dorsal sepal — Glabrous, velvety, and matte. Lateral sepals — Glabrous, velvety, and matte. Color when opening, upper surface — Dorsal sepal — Purple, nearest to in between RHS 76C and 76D, and darker towards the apex, in between RHS 77C and 77D; reticulate venation is purple, nearest to RHS N75A, and darker towards the apex, in between RHS N78B and N78C. Lateral sepals — Purple, nearest to RHS 75D, and darker towards the apex, in between RHS 77C and N78C; base is suffused with greyed-yellow, nearest to RHS 160D; reticulate venation is purple, nearest to RHS N75A, and darker towards the apex, in between RHS N78B and N78C. Color when opening, lower surface — Dorsal sepal — Purple, nearest RHS 76D, and darker towards the apex, in between RHS 77C and 77D; reticulate venation is purple, nearest to RHS N78D, and darker towards the apex, in between RHS N78B and N78C. Lateral sepals — Purple, nearest RHS 76D, and darker towards the apex, in between RHS 77C and 77D; base is suffused with greyed-yellow, nearest to RHS 160D; reticulate venation is purple, nearest to RHS N78D, and darker towards the apex, in between RHS N78B and N78C. Color when fully opened, upper surface — Dorsal sepal — Purple, nearest to RHS 76C, and fading to purple-violet towards the margins and apex, nearest to RHS N80A; base is purple, RHS N78B. Lateral sepals — Purple, nearest to RHS 76D, and darker towards the margins and apex, in between RHS 77B and N78B; base is suffused with greyed-yellow, nearest to RHS 160D. Color when fully opened, lower surface — Dorsal sepal — Purple, nearest to RHS 76D, and darker towards the apex, in between RHS N78B, N78C, and N78D. Lateral sepals — Purple, nearest to RHS 76C, and darker towards the margins and apex, in between RHS N78B and N78C; base is suffused with orange-white, nearest to RHS 159D. Fading, upper surface — Not fading. Fading, lower surface — Not fading. Venation — Densely reticulate. Venation color, fully opened, upper surface — Dorsal sepal — Purple, nearest to RHS N78C, and darker towards the apex, nearest to RHS N78B. Lateral sepals — Purple, nearest to RHS N78C, and darker towards the apex, nearest to RHS N78B. Venation color, fully opened, lower surface — Dorsal sepal — Purple, nearest to RHS N78C, and darker towards the apex, in between RHS N78B and N78C. Lateral sepals — Purple, nearest to RHS N78C, and darker towards the apex, in between RHS N78B and N78C.

*Pedicels*.—Length — Approximately 4.9 cm. Diameter — Approximately 0.35 cm. Angle — Approximately 65 degree angle to peduncle axis. Strength — Moderate. Texture — Glabrous, axially angled with 5 "ribs", axially twisted (due to resupination). Luster — Glossy. Color — Purple, nearest to RHS 76B; fading to yellow-green, in between RHS 145B and 145C; fading to yellow-green, nearest to RHS 150D, towards the distal end.

*Bract*.—Quantity — One bract present at the base of each pedicel. Shape — Reniform; folded around the base of each pedicel. Dimensions — Average of 1.0 cm long and 0.7 cm wide. Apex — Broad acute. Base — Broad cuneate. Margins — Entire. Color, both surfaces — Yellow-green, nearest to RHS N144D.

Reproductive organs:

*Column*.—Length — Approximately 0.5 cm. Diameter — Approximately 0.6 cm. Color — Purple, nearest to in between RHS 77B and 77C.

*Ovary*.—Position — Inferior. Diameter — Approximately 1.0 cm. Color — Yellow-green, nearest to RHS 150C.

*Pollinia color*.—No pollinia present.

Seed and fruit: No fruit and seed production has been detected to date.

Comparison with the parent plant:

Plants of the new cultivar 'SPCDW1602' differ from the *Vanda* parent, 'SPCDW0902' (not patented), by the characteristics described in Table 1.

TABLE 1

| Characteristic | 'SPCDW1602' | 'SPCDW0902' |
|---|---|---|
| General coloration of the petals and sepals when fully opened. | Pink. | White. |
| Color pattern on the petals and sepals. | Netted. | None. |

Comparison with the most similar *Vanda* cultivar known to the inventor:

Plants of the new cultivar 'SPCDW1602' are most similar to the cultivar, *Vanda* 'SPCDW1307' (not protected in the United States; Community Plant Variety Rights grant number 39337). A comparison of 'SPCDW1602' with *Vanda* 'SPCDW1307' is described in Table 2.

TABLE 2

| Characteristic | 'SPCDW1602' | 'SPCDW1307' |
|---|---|---|
| Leaf color. | Lighter green. | Darker green. |
| General coloration of the petals when fully opened. | Light pink with dark purple reticulate venation. | Darker pink with dark purple reticulate venation. |
| General coloration of the central lobe of the labellum. | Lighter pink. | Darker pink. |
| General coloration of the column. | Lighter pink. | Darker pink. |

That which is claimed is:

1. A new and distinct variety of *Vanda* plant named 'SPCDW1602', substantially as described and illustrated herein.

* * * * *